(12) United States Patent
Rutledge

(10) Patent No.: US 8,403,933 B2
(45) Date of Patent: Mar. 26, 2013

(54) LOCKING CAP DISPENSER

(75) Inventor: Henry Rutledge, West Chester, PA (US)

(73) Assignee: Synthes USA, LLC, West Chester, PA (US)

( * ) Notice: Subject to any disclaimer, the term of this patent is extended or adjusted under 35 U.S.C. 154(b) by 56 days.

(21) Appl. No.: 13/107,588

(22) Filed: May 13, 2011

(65) Prior Publication Data
US 2012/0290012 A1 Nov. 15, 2012

(51) Int. Cl.
A61B 17/70 (2006.01)
A61B 17/88 (2006.01)

(52) U.S. Cl. .................. 606/86 A; 606/104; 606/279

(58) Field of Classification Search ............... 606/86 A, 606/86 B, 99, 914–916; 81/9.24, 57.37, 81/431, 434
See application file for complete search history.

(56) References Cited

U.S. PATENT DOCUMENTS

| | | | |
|---|---|---|---|
| 2,247,500 A | 7/1941 | Hutchinson, Jr. | |
| 2,868,053 A | 1/1959 | Jorgensen et al. | |
| 3,971,421 A * | 7/1976 | Damratowski | 81/434 |
| 4,018,254 A * | 4/1977 | DeCaro | 81/57.37 |
| 5,167,174 A * | 12/1992 | Fujiyama et al. | 81/434 |
| 5,339,713 A * | 8/1994 | Hou | 81/434 |
| 5,957,927 A * | 9/1999 | Magee et al. | 606/99 |
| 6,595,998 B2 * | 7/2003 | Johnson et al. | 606/90 |
| 6,676,001 B1 * | 1/2004 | Chen et al. | 227/119 |
| 6,701,811 B1 * | 3/2004 | Chang et al. | 81/434 |
| 7,481,813 B1 * | 1/2009 | Purcell | 606/86 R |
| 7,691,129 B2 | 4/2010 | Felix | |
| 2003/0225408 A1 * | 12/2003 | Nichols et al. | 606/61 |
| 2007/0093849 A1 | 4/2007 | Jones et al. | |
| 2007/0213722 A1 * | 9/2007 | Jones et al. | 606/61 |
| 2008/0255576 A1 | 10/2008 | Protopsaltis | |
| 2008/0264218 A1 * | 10/2008 | Wang et al. | 81/434 |
| 2009/0163962 A1 | 6/2009 | Dauster et al. | |
| 2011/0040335 A1 | 2/2011 | Stihl et al. | |

FOREIGN PATENT DOCUMENTS

WO 2008/097974 8/2008

OTHER PUBLICATIONS

European Search Report (EP 12 16 7870); Jul. 20, 2012.

* cited by examiner

Primary Examiner — Eduardo C Robert
Assistant Examiner — Julianna N Harvey
(74) Attorney, Agent, or Firm — Dunlap Codding, P.C.

(57) ABSTRACT

An apparatus for dispensing a plurality of locking caps including a barrel and a magazine. The barrel has a longitudinal passage extending through the barrel and a lateral passage extending through the barrel and intersecting the longitudinal passage. A second open end of the barrel is configured to engage a rod receiving head to which one of the locking caps is threadingly connectable. The magazine has a housing with a chamber for receiving a plate carrying a plurality of locking caps. The chamber of the housing is aligned with the lateral passage of the barrel so that the plate is movable from the chamber into the lateral passage so that one of the locking caps is positioned in the longitudinal passage so as to be matingly engageable with a drive tool insertable through the longitudinal passage.

19 Claims, 19 Drawing Sheets

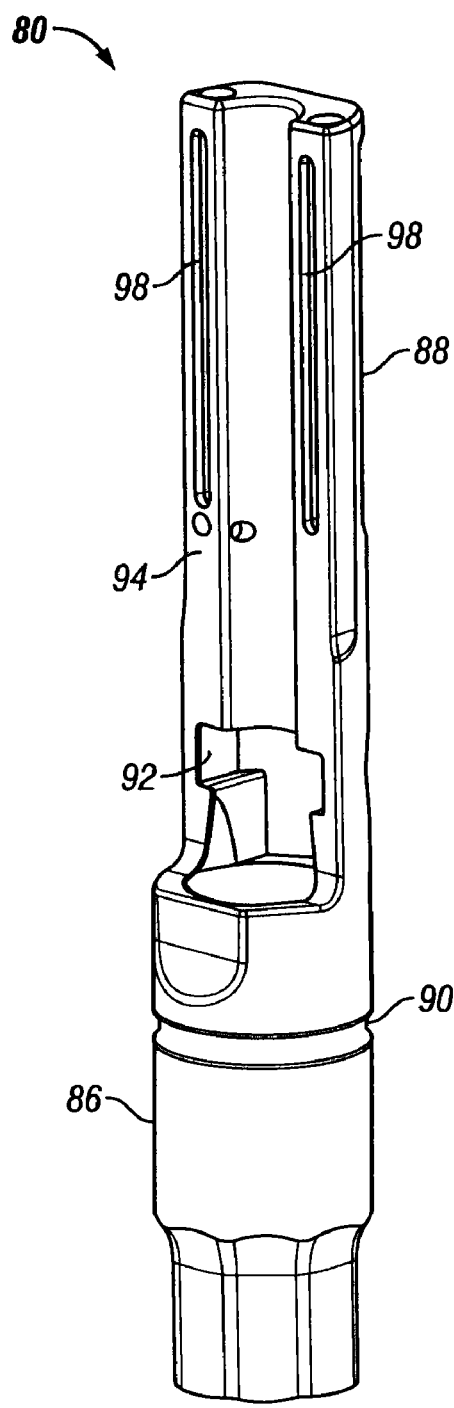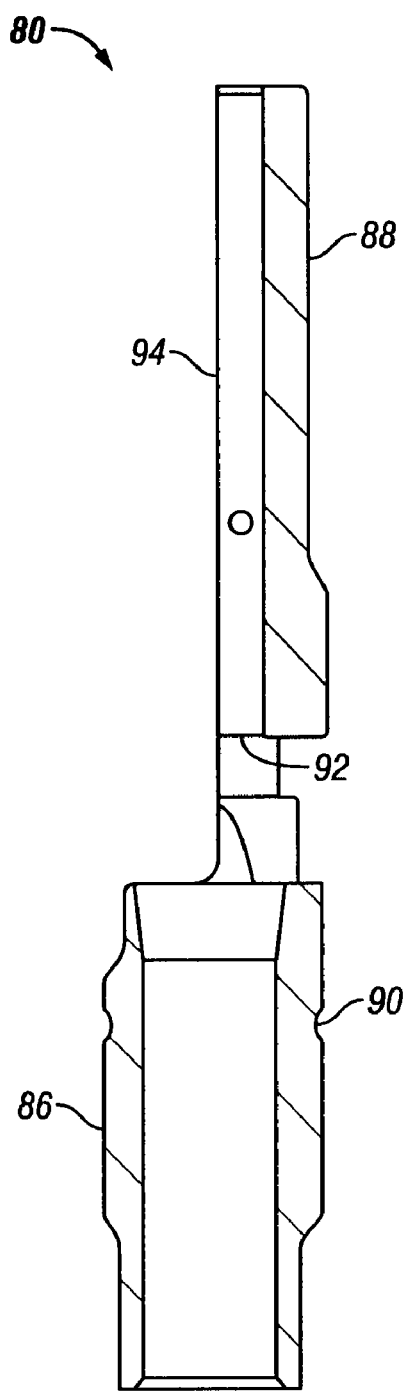
FIG. 5    FIG. 6

LOCKING CAP DISPENSER

BACKGROUND OF THE PRESENTLY DISCLOSED AND/OR CLAIMED INVENTIVE CONCEPTS

1. Field of the Presently Disclosed and/or Claimed Inventive Concepts

The inventive concepts disclosed and claimed herein relate to instruments for fixing orthopedic implants, and more particularly, but not by way of limitation, to an apparatus for dispensing multiple implants and applying a counterforce.

2. Brief Description of Related Art

Several techniques and systems have been developed for correcting and stabilizing the spine and for facilitating fusion at various levels of the spine. Stabilization of the spine for various conditions, including degenerative disk disease, scoliosis, spondylolisthesis, and spinal stenosis, often require attaching implants to the spine and then securing the implants to spinal rods. Such spinal fixation devices can immobilize the vertebrae of the spine and can alter the alignment of the spine over a large number of vertebrae by connecting at least one elongate rod to the sequence of selected vertebrae. These rods can span a large number of vertebrae, such as three or four. The spine anatomy, however, rarely allows for three or more implants to be directly in line. In order to allow for this irregularity, the rod must be contoured to the coronal plane.

Spinal fixation has become a common approach in fusion of vertebrae and treating fractures and the above listed spinal disorders. A common device used for spinal fixation is a bone fixation plate assembly. Typical bone fixation plate assemblies have a relatively flat, rectangular plate with a plurality of apertures therethrough. Another option is an implantation fixation system that locks a rod to several vertebrae. In these systems, as with other spinal fixation systems, various fasteners, such as bone screws, are used to secure the implantation fixation assembly to the desired and targeted vertebrae of the patient. These screws vary in design and shape depending upon their desired location and use.

Polyaxial locking screws are frequently used as fasteners in implantation fixation systems. Once these screws are set in a desired position, the screws are securely fixed in that position to minimize or eliminate movement of the screws. This is typically accomplished with a fixation system that securely engages the polyaxial screw.

There are numerous polyaxial screws and fixation systems existing in the market today. Some fixation systems utilize a rod receiving head having a central passage, and a polyaxial screw inserted into the central passage. The screw has a head portion that seats inside one end of the rod receiving head, and a threaded shank that projects through the end of the rod receiving head in an exposed manner. An elongated rod is seated in the rod receiving head and extends transversely through the central passage. The rod is secured in the rod receiving head with a threaded locking cap that is screwed around the exterior of the rod receiving head or in the interior of the rod receiving head to lock the rod in place.

Locking caps are typically inserted into the rod receiving head with an instrument that has been loaded with a single locking cap. Consequently, after one locking cap is threaded into the rod receiving head with the instrument, a surgeon is handed another instrument loaded with another locking cap, or the same instrument is passed to a technician who loads the same instrument with another locking cap and passes back to the surgeon. The application of the locking caps continues in this back and forth fashion until all the locking caps are threaded and secured into position, and thus the application of the locking caps is a time consuming process.

Another characteristic of the locking cap application process is that the torque applied to the locking caps is transferred to the rod receiving head and polyaxial screw. More specifically, a significant amount of torque is typically applied in the final tightening. This introduces a risk of "blowout," in which torque or other components of force tilt the shank out of its set alignment in the screw hole causing the shank to break through the relatively thin bone wall of the pedicle. In such a case, removal and resetting of the polyaxial screw can exacerbate the trauma to the bone.

To control the risk of blowout, some practitioners use additional instrumentation to apply a countertorque to the fixation mechanism, so that the torque applied to locking cap does not cause rotation or displacement of the locking cap and polyaxial screw. This requires the careful balancing of torque with countertorque, and any imbalance can still cause blowout. Moreover, application of countertorque requires an additional instrument to be used at the same time that the locking cap is being driven into the cage. Aside from the obvious disadvantage of adding to instrument costs and instrument preparation, the countertorque instrument can be cumbersome to use while advancing the locking cap at the same time.

To this end, a need exists for an improved apparatus and method for delivering multiple locking caps while minimizing the time associated with handling and tightening such locking caps during surgery. It is to such an apparatus and method that the inventive concepts disclosed and claimed herein are directed.

BRIEF DESCRIPTION OF THE DRAWINGS

FIG. 5 is a perspective view of a barrel base.

FIG. 6 is a sectional view of the barrel base of FIG. 5.

DETAILED DESCRIPTION OF EXEMPLARY EMBODIMENTS

Figure 1:
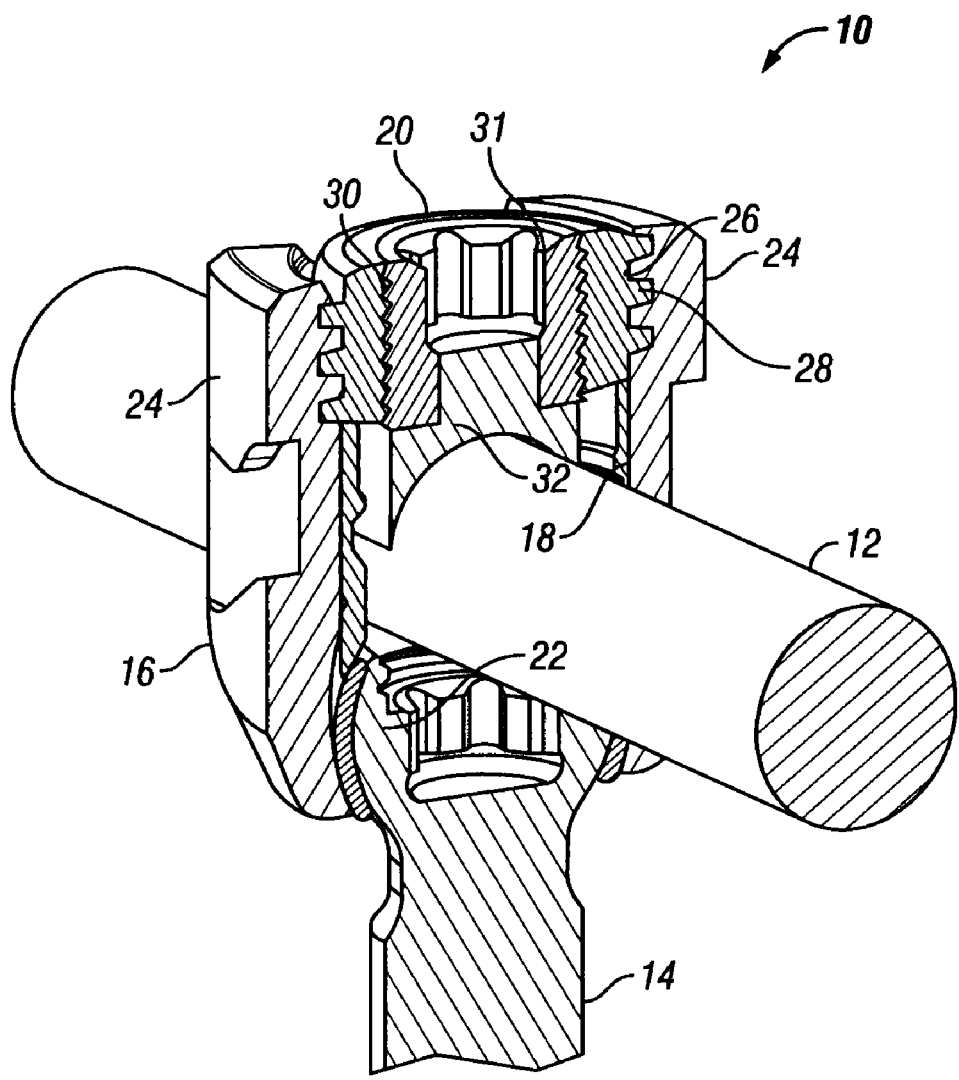
FIG. 1 is a perspective view of a prior art bone fixation element including a locking cap.

Before explaining at least one embodiment of the presently disclosed and claimed inventive concepts in detail, it is to be understood that the presently disclosed and claimed inventive concepts is not limited in its application to the details of construction, experiments, exemplary data, and/or the arrangement of the components set forth in the following description or illustrated in the drawings. The presently disclosed and claimed inventive concepts are capable of other embodiments or of being practiced or carried out in various ways. Also, it is to be understood that the phraseology and terminology employed herein is for purpose of description and should not be regarded as limiting.

Referring now to the drawings, FIG. 1 illustrates an exemplary embodiment of a bone fixation element 10 for use in a posterior spinal fixation procedure to interconnect a longitudinal rod 12 with a patient's vertebra. Broadly, the bone fixation element 10 includes a bone anchor 14 for securing the bone fixation element 10 to a patient's vertebra, a rod receiving head 16 having a rod-receiving channel 18 for receiving the rod 12, and a locking cap 20 for securing the rod 12 in the rod-receiving channel 18 in an implanted configuration. The bone anchor 14 is shown to include an enlarged head portion 22 which is received within an inner spherical cavity formed in rod receiving head 16 so that the bone anchor 14 can poly-axial rotate with respect to the rod receiving head 16. Alternatively, the bone anchor 14 may be formed integral with the rod receiving head 16 to form a monolithic structure which is referred to as a mono-axial pedicle screw or hook.

The rod receiving head 16 has a pair of arms 24 which define the rod receiving chamber 18. The arms 24 include a plurality of threads 26 on an inner surface thereof for threadably receiving the locking cap 20.

The locking cap 20 is shown to be in the form of a two step locking cap including an externally threaded outer part 28 with an internal bore 30 for threadably receiving an externally threaded inner part 30. A saddle 32 is coupled to the inner part 30 of the locking cap 20. The saddle 32 is rotatably coupled to the inner part 30 so that the saddle 32 can contact the top surface of the rod 12 while the locking cap 20 is being threaded with the rod receiving head 16.

Exemplary embodiments of pedicle screws include those described in International Patent Application No. PCT/US2008/070670, filed on Jul. 21, 2008, entitled "Polyaxial Bone Fixation Element," International Patent Application No. PCT/US2006/015692, filed on Apr. 25, 2006, entitled "Bone Anchor with Locking Cap and Method of Spinal Fixation," and International Patent Application No. PCT/CH1997/00236, filed on Jun. 16, 1997, entitled "Device for Connecting a Longitudinal Support with a Pedicle Screw," the contents of which are hereby incorporated by reference in their entirety. It should be understood however that the present invention is not limited in use to any particular type of locking cap or pedicle screw.

As described above, the process of securing the locking caps 20 to the rod receiving head 16 is a tedious and time consuming process. To this end, a need exists for an improved apparatus and method for delivering multiple locking caps while minimizing the time associated with handling and tightening such locking caps during surgery.

Figure 2:
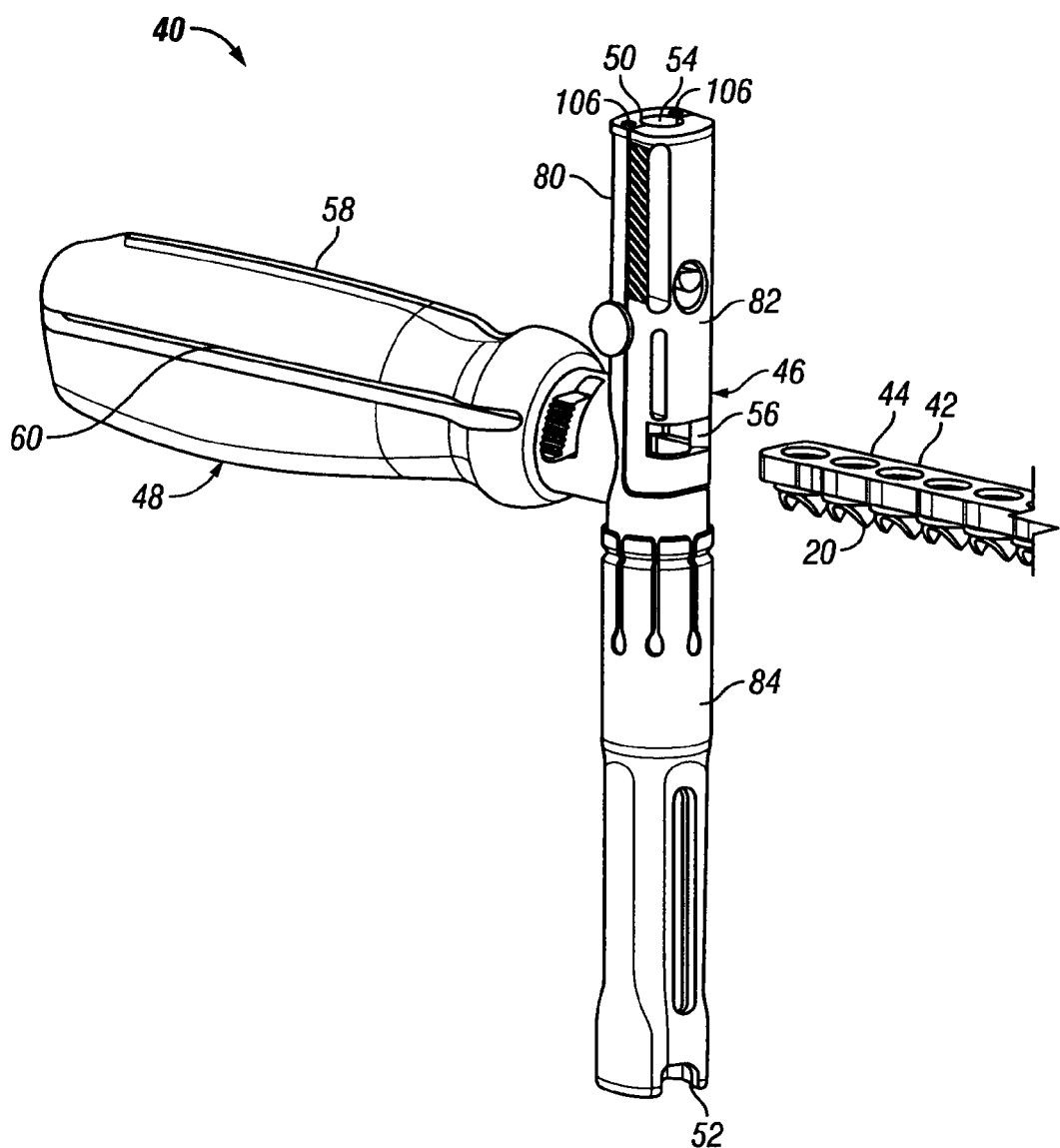
FIG. 2 is a perspective view of a locking cap dispenser and locking cap clip constructed in accordance with the inventive concepts disclosed and claimed herein.

FIG. 2 illustrates one embodiment of a locking cap dispenser 40 and a locking cap clip 42 for use with the locking cap dispenser 40. In one embodiment, the locking cap clip 42 includes a plate 44 and a plurality of locking caps 20 threaded to the plate 44. Broadly, the locking cap dispenser 40 includes a barrel 46 and a magazine 48 extending substantially perpendicularly from the barrel 46. The barrel 46 has a first open end 50, a second open end 52, and a longitudinal passage 54 extending through the barrel 46 from the first open end 50 to the second open end 52. The second open end 52 of the barrel 46 is configured to engage the rod receiving head 16 (FIGS. 1 and 23-25). The barrel 46 further has a lateral passage 56 extending through the barrel 46 and intersecting the longitudinal passage 54.

The magazine 48 has a housing 58 with a chamber 60 for receiving the locking cap clip 12. The housing 58 extends from the barrel 46 with the chamber 60 of the housing 58 aligned with the lateral passage 56 of the barrel 46 so that the plate 44 of the locking cap clip 42 is movable from the chamber 58 of the housing 58 into the lateral passage 56 of the barrel 46 in such a way that one of the locking caps 20 is positioned in the longitudinal passage 54 of the barrel 46 so as to be matingly engageable with a drive tool 62 (FIGS. 23 and 24) insertable through the longitudinal passage 54 to permit the drive tool 62 to be used to detach the locking cap 20 from the plate 44 and transport the detached locking cap 20 to the second open end 52 of the barrel 46 where the drive tool 62 can be used to thread the locking cap 20 to the rod receiving head 16.

Figure 3A:
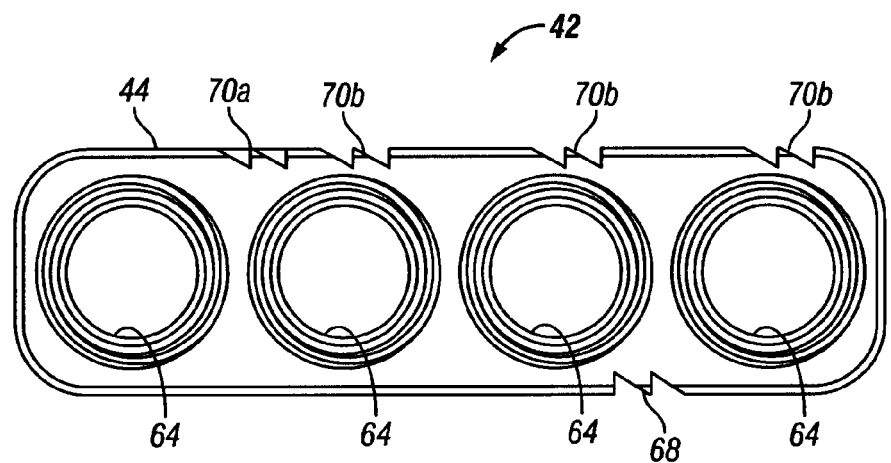
FIG. 3A is a top plan view of the locking cap clip.
Figure 3B:
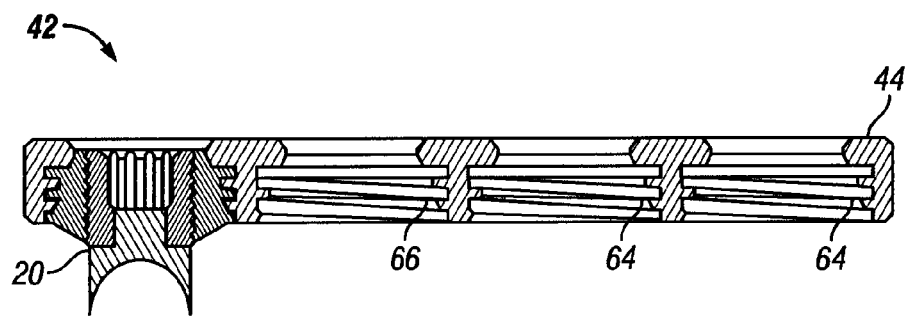
FIG. 3B is a sectional view of the locking cap clip shown with one locking cap.
Figure 4:
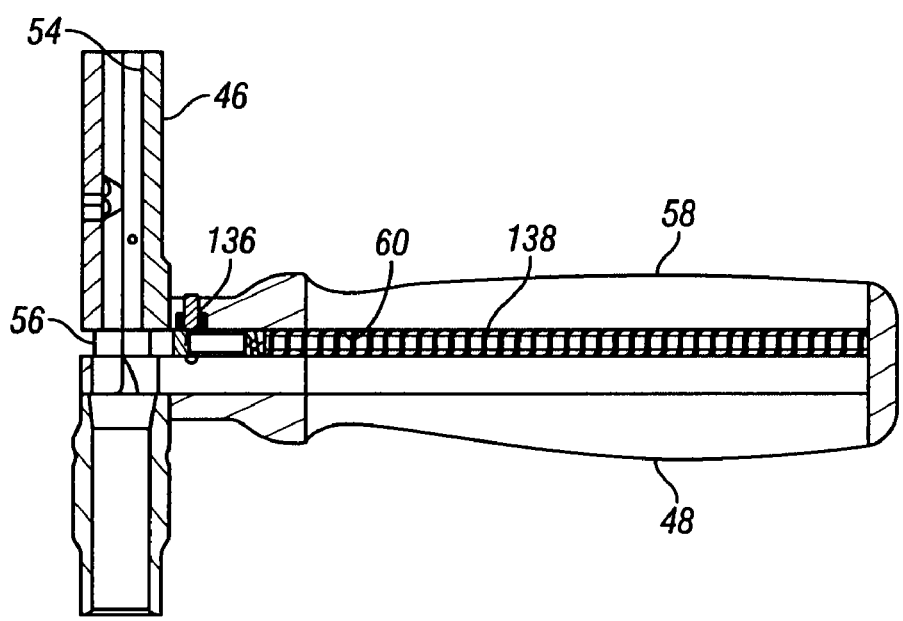
FIG. 4 is a cross-sectional view of the locking cap dispenser.
Figure 7:
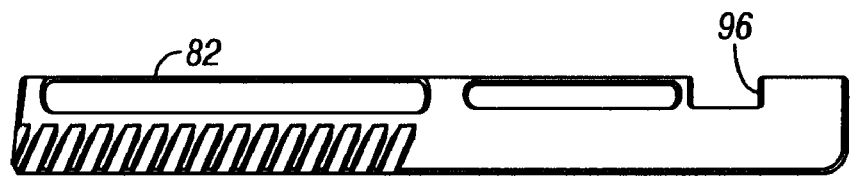
FIG. 7 is a side elevational view of a slide member.
Figure 8A:
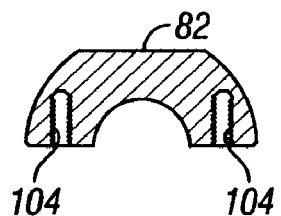
FIG. 8A is a top plan view of the slide member of FIG. 7.
Figure 8B:
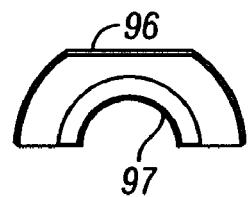
FIG. 8B is a cross-sectional view taken along line 8B-8B in FIG. 7.
Figure 9:
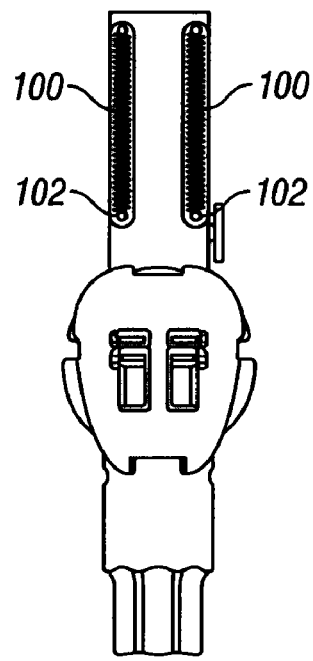
FIG. 9 is a rear elevational view of the locking cap dispenser.

Referring now to FIGS. 3A and 3B, the locking cap clip 42 of FIG. 1 is shown in more detail. More particularly, the plate 44 is shown to have an elongated configuration and to include a plurality of openings 64 spaced apart along a longitudinal axis of the plate 44. As best shown in FIG. 3B, a lower portion of the openings 64 is provided with threads 66 for threadably connecting the locking caps 20 to the plate 44. An upper portion of the openings 64 is tapered to facilitate engagement of the drive tool 62 with the locking cap 20 in a manner to be described below. It will be appreciated by those of ordinary skill in the art that shape and size of the plate 44 and the number of openings provided therein may be varied.

As show in FIG. 3A, the plate 44 may include a latching area 68 formed on one side of the plate 44 and a plurality of latching areas 70a and 70b formed along an opposing side of the plate 44 to permit the locking cap clip 42 to be advanced through the magazine in either an automatic mode or a semi-automatic mode. As will described in greater detail below, the latching area 68 is positioned to cooperate with the magazine 48 to hold the locking cap clip 12 in a selected position when the locking cap clip 12 is positioned within the magazine 46 in one orientation (automatic) and the latching areas 70a and 70b are positioned to cooperate with the magazine 48 to hold the locking cap clip 12 in selected positions when the locking cap clip 12 is positioned within the magazine 46 in a different orientation (semi-automatic). In one embodiment, the latching areas 68, 70*a*, and 70*b* include a pair of angled notches. The latching areas 70*b* are positioned to correspond with one of the openings 64 of the plate 44.

Referring now to FIGS. 2 and 4-14, in one embodiment the barrel 46 includes a barrel base 80, a slide member 82, and an extension member 84. As shown in FIGS. 5 and 6, the barrel base 80 includes a first portion 86 and a second portion 88. The first portion 86 is generally tubular so as to define a portion of the longitudinal passage 54 of the barrel 46. The first portion 86 further includes an annular groove 90 for interlocking the extension member 84 with the barrel 46 in a manner to be described below. The second portion 88 of the barrel base 80 has an opening 92 defining a first portion of the lateral passage 56. The opening 92 is preferably generally T-shaped to correspond with the shape of the locking cap clip 42, including the plate 44 and the locking caps 20, and thus permit the locking cap clip 42 to pass through the opening 92. The second portion 88 further has an open side portion 94 sized to allow the locking cap clip 12 to be passed through the open side portion 94 to permit the locking cap clip 12 to be loaded into the magazine 46 in a manner to be described below. The second portion 88 is shown to be generally semicircular in shape, but it should be appreciated the second portion 88 may be configured in a variety of functional configurations.

Figure 22:
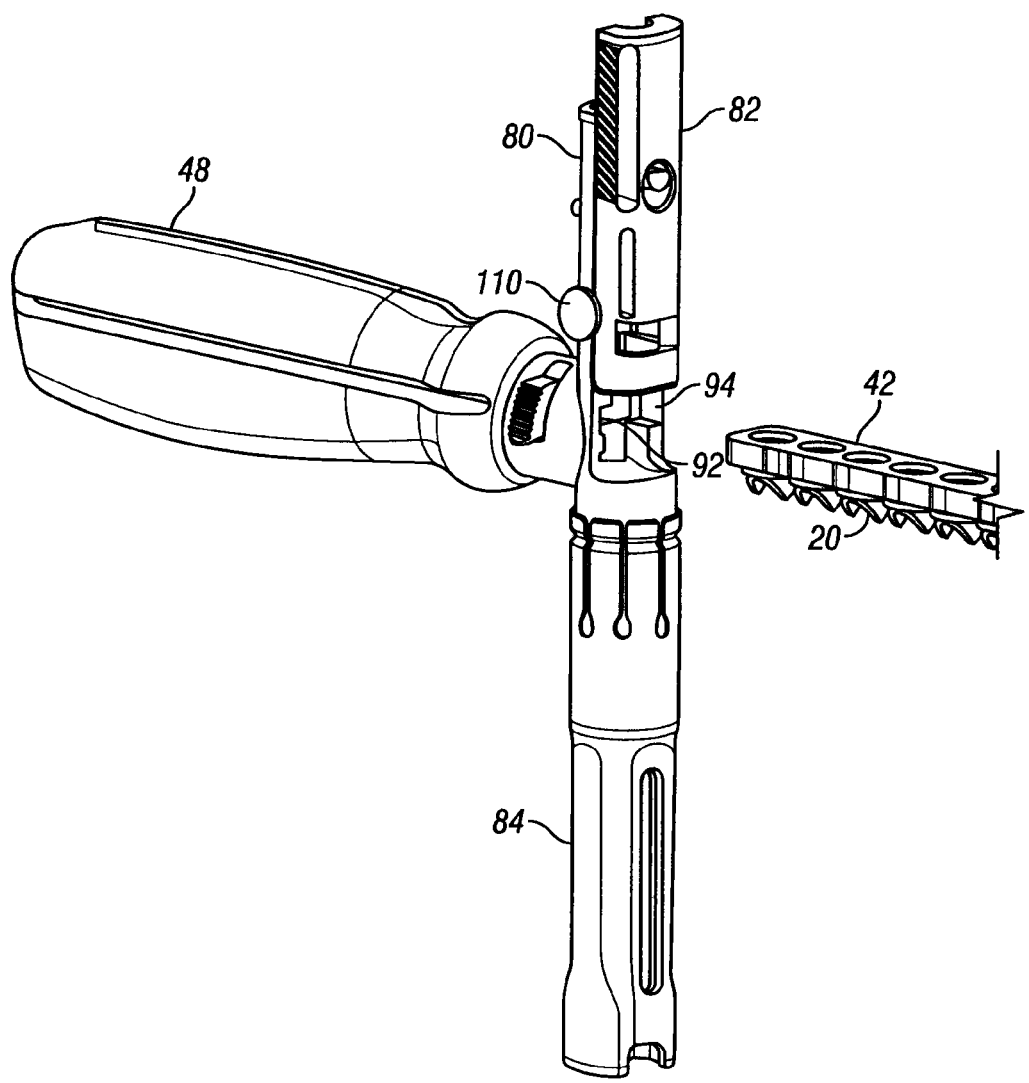
FIG. 22 is a perspective view of the locking cap dispenser showing the slide member in the open position.
Figure 23:
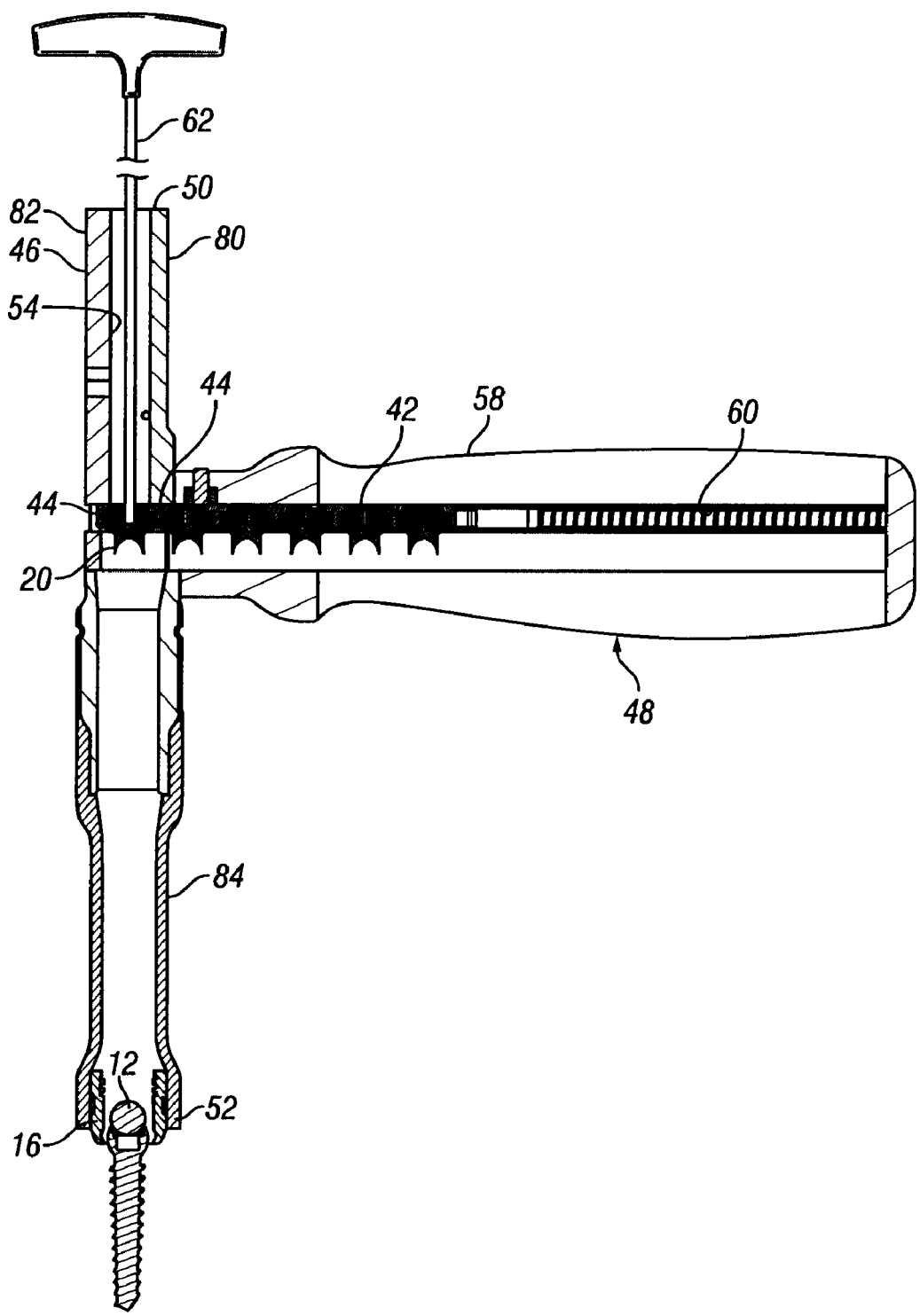
FIG. 23 is a sectional view of the locking cap dispenser shown engaging a rod receiving head and shown with a drive tool engaging a locking cap.

Referring now to FIGS. 7-12, the slide member 82 is generally sized and shaped to cover the open side portion 94 of the barrel base 80. The slide member 82 has an opening 96 defining a second portion of the lateral passage 56 of the barrel 46. The opening 96 is preferably sized and shaped to permit only the plate 44 to pass there through. The slide member 82 is connected to the barrel base 80 in such a way that the slide member 82 is movable along the barrel base 80 between an open position (FIG. 22) wherein at least a portion of the open side portion 94 of the barrel base 80 is exposed to permit the locking cap clip 42, including the plate 44 and the locking caps 20, to be inserted through the open side portion 94 of the barrel base 80, through the opening 92 of the barrel base 80, and into the chamber 60 of the housing 58 and a closed position (FIGS. 1 and 4) wherein the slide member 82 is positioned to cover the open sided portion 94 of the barrel base 80 and the opening 96 of the slide member 82 is aligned with the upper horizontal portion of the opening 92 of the barrel base 80. An interior surface 97 (FIG. 8B) of the slide member 82 which is located between the opening 96 and the lower end of the slide member 82 is preferably dimensioned to function as a stop so that when a locking cap 20 is in contact with the interior surface 97, the locking cap 20 is in alignment with the longitudinal passage 54 of the barrel 46.

To effect the slidable connection between the slide member 82 and the barrel base 80, in one embodiment the barrel base 80 is provided with a pair of longitudinal slotted holes 98 (FIG. 5) which are open at the distal end of the barrel base 80 to permit a spring 100 (FIG. 9) to be disposed in each of the slotted holes 98. The springs 100 are supported on a lower end by a fastener, such as a slide bolt 102, disposed transversely through the slotted holes 98 and secured to threaded openings 104 (FIG. 8A) of the slide member 82. The springs 100 may be secured within the slotted holes 98 with setscrews 106 (FIG. 2). With the springs 100 secured in the slotted holes 98, the slide member 82 is biased in the closed position. When the slide member 82 is moved to an open position, the slide bolts 102 slide along the slotted holes 98 and cause the springs 100 to be compressed.

Figure 10:
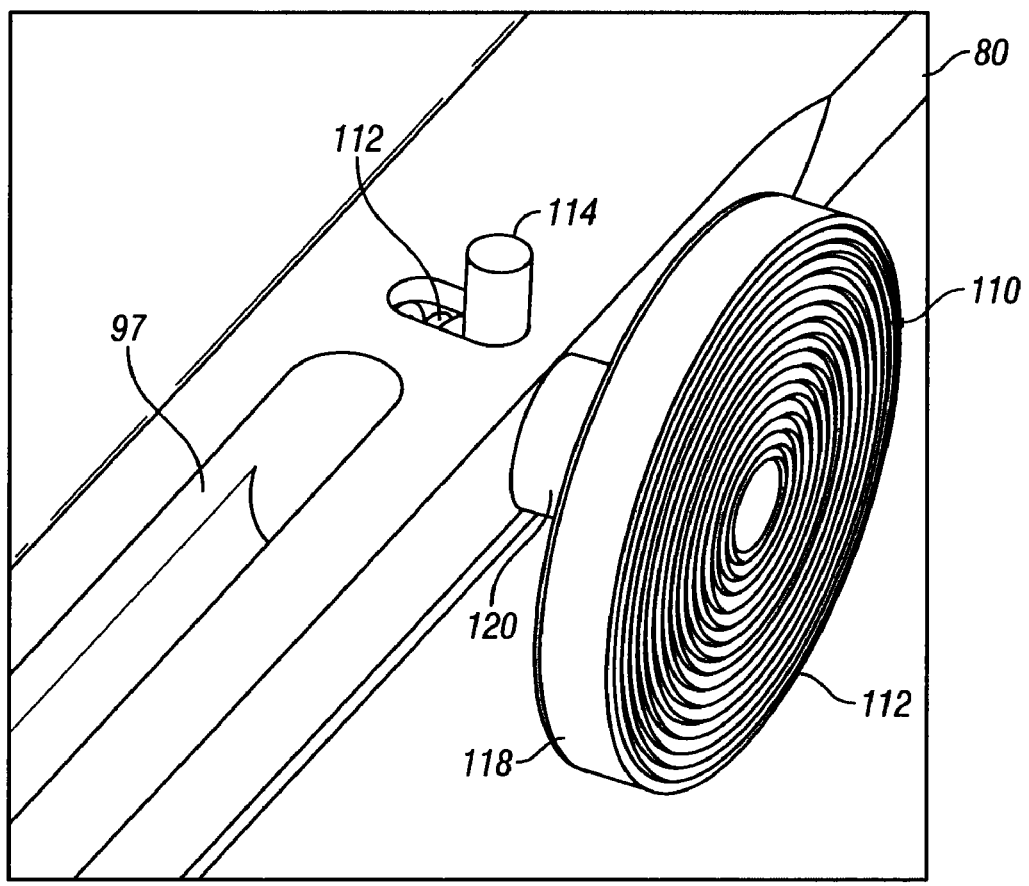
FIG. 10 is a perspective view showing a slide lock assembly.
Figure 11:
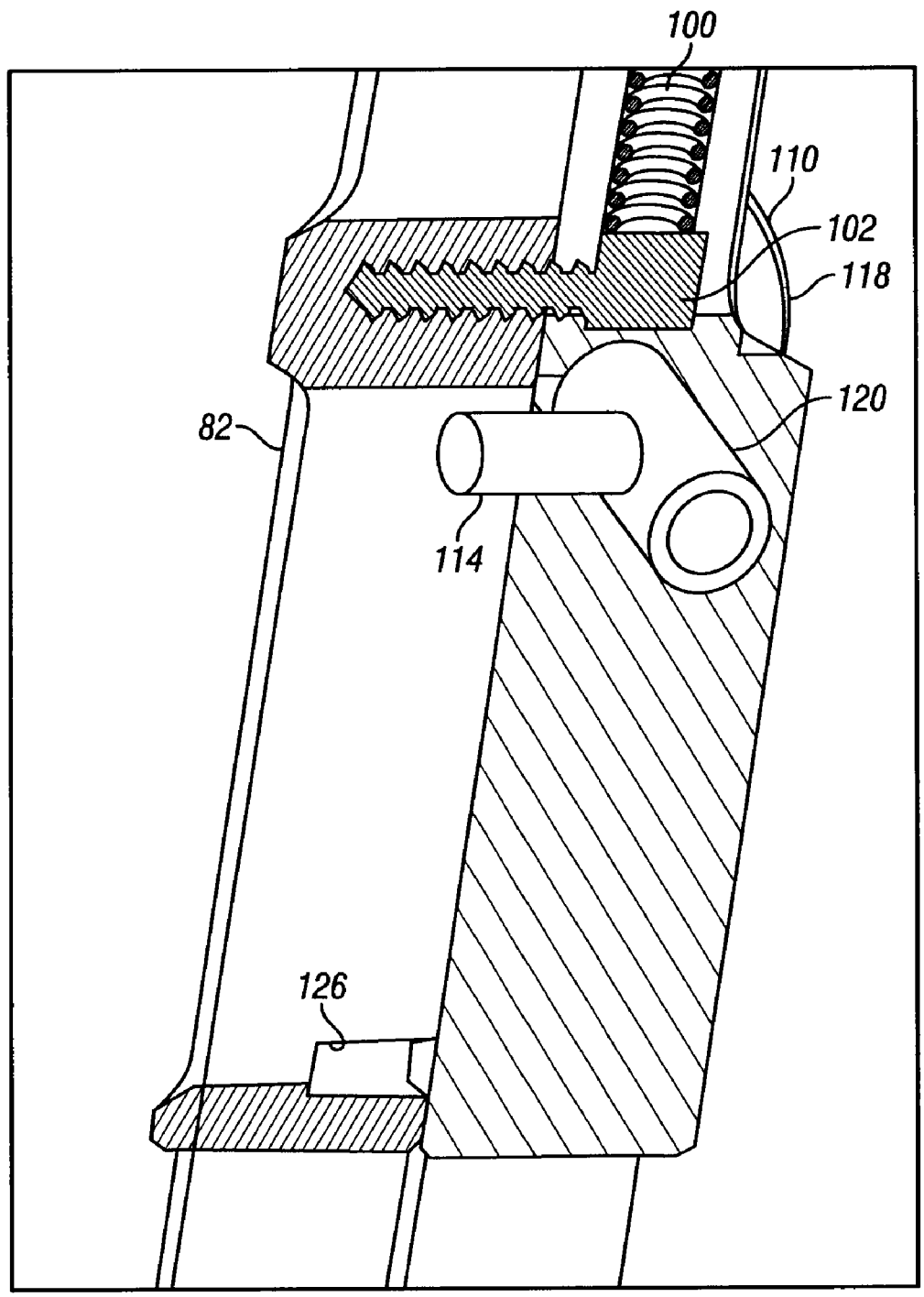
FIG. 11 is a perspective view of a portion of the slide member shown in a closed position.
Figure 12:
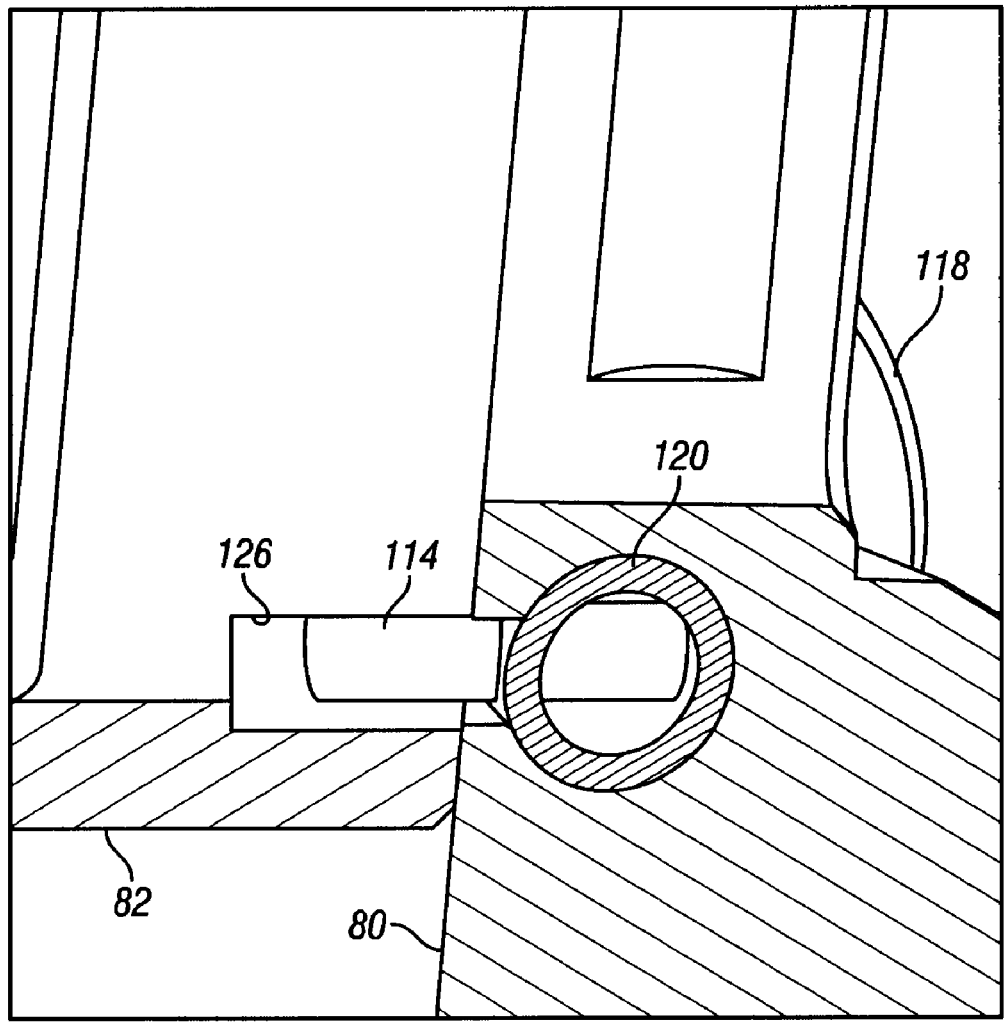
FIG. 12 is a perspective view of a portion of the slide member shown in an open position.

To support the slide member 82 in the open position, the barrel base 80 is provided with a slidelock assembly 110, as illustrated in FIGS. 10-12. The slidelock assembly 110 comprises a slidelock 112, a press pin 114 extending from the slidelock 112, and a spring 116 for biasing the combination of the slidelock 112 and the press pin 114 in an outward direction. The slidelock 112 has a knob 118 formed on one end of a shaft 120. The shaft 120 is disposed in a hole 122 formed in one side of the barrel base 80. The barrel base 80 includes an elongated slot 124 through which the press pin 114 extends. The press pin 114 is biased against the slide member 82 when the slide member 82 is in any position other than a fully open position. In the fully open position, the press pin 114 engages a slot 126 (FIG. 12) formed in the slide member 82 to latch the slide member 82 to the barrel base 80 and thereby support the slide member 82 in the open position. To move the slide member 92 from the open position, the knob 118 of the slidelock 112 is pushed inwardly to cause the press pin 114 to disengage from the slot 126.

Figures 13, 14:
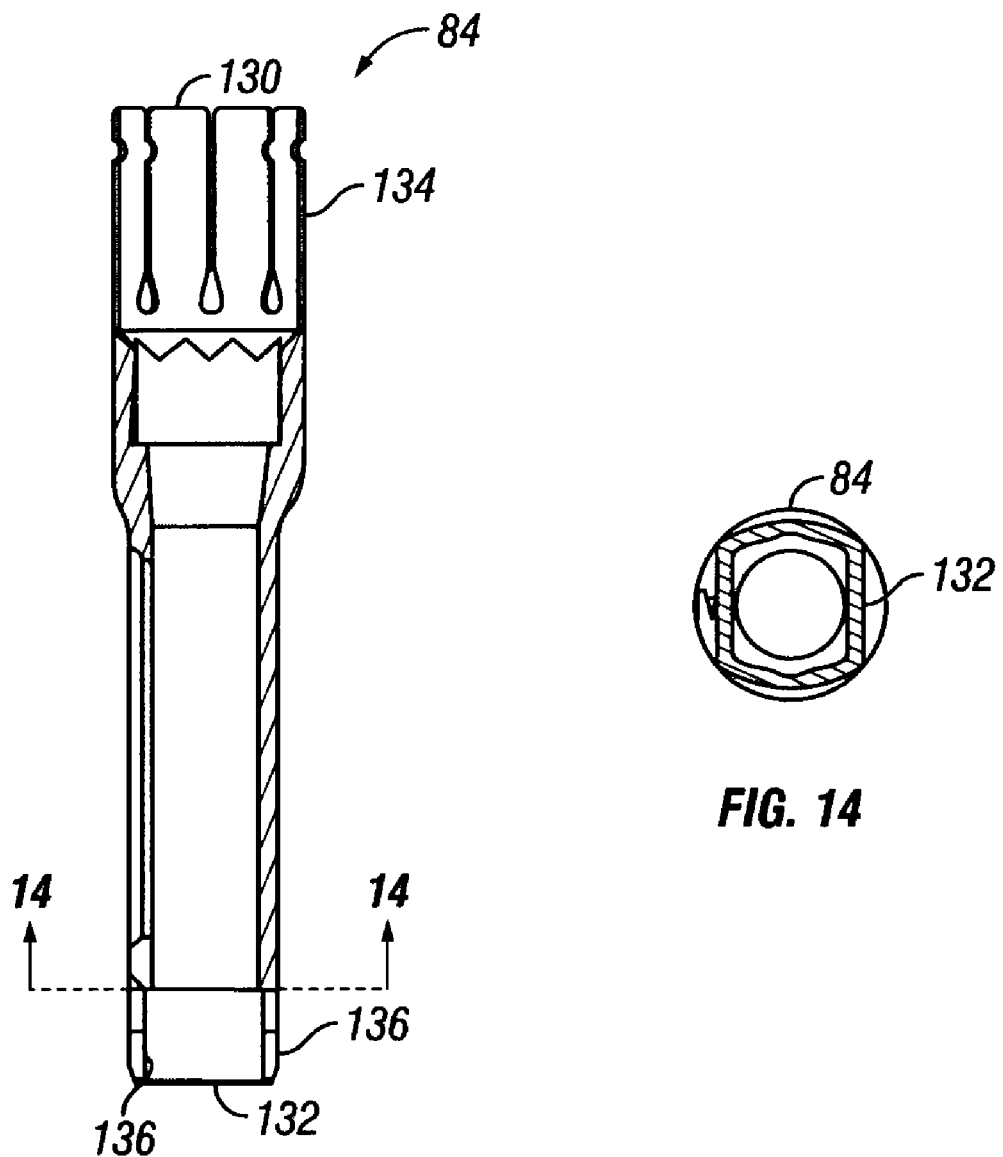
FIG. 13 is a sectional view of a barrel extension member.
FIG. 14 is a cross-sectional view taken along line 14-14 of FIG. 13.
Figure 15:
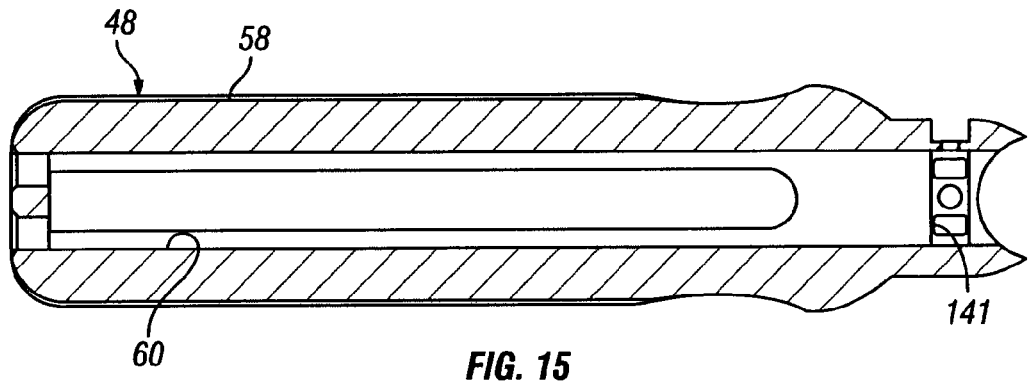
FIG. 15 is a sectional view of a magazine.
Figure 16:
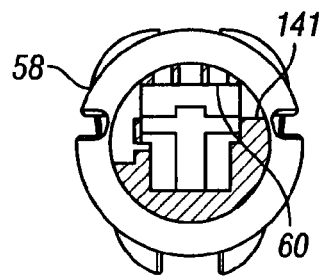
FIG. 16 is a cross-sectional view taken along line 16-16 of FIG. 15.

Referring now to FIGS. 13 and 14, the extension member 84 is a tubular member having a proximal end 130 detachably connected to the first portion 86 of the barrel base 80 and a distal end 132 defining the second open end 52 of the barrel 46. It will be appreciated by those of ordinary skill in the art that the extension member 84 may be formed with the barrel base 80 so as to form a monolithic structure. However, by the extension member 84 being a separate piece, a surgeon may select an extension member with a length suited for the anatomy of the patient.

The proximal end 130 of the extension member 84 is configured to be slid over the first portion 86 of the barrel base 80. To this end, the barrel base 80 and the proximal end 130 of the extension member 84 are provided with corresponding geometry. In one embodiment, the barrel base 80 and the proximal end 130 of the extension member 84 are each provided with an octagonal geometry to permit the surgeon to rotate the extension member 84 to various positions relative to the barrel base 80, depending on the surgeon's preference. The proximal end 130 is provided with a plurality of fingers 134 that are engageable with the annular groove 90 of the barrel base 80 to detachably connect the extension member 84 to the barrel base 80.

As best shown in FIG. 14, the distal end 132 of the extension member 84 is configured to engage the rod receiving head 16 (FIGS. 1 and 23-25) so that the locking cap dispenser 40 may be used to apply a counterforce to the rod receiving head 16 in a manner to be discussed below. The distal end 132 is further provided with a pair of opposing slots 136 for receiving the rod 12 when the distal end 132 is engaged with the rod receiving head 16.

Referring now to FIGS. 15-21 and as described above, the housing 58 of the magazine 48 includes the chamber 60 configured to slidably receive the locking cap clip 42. The chamber 60 is substantially T-shaped with the plate 44 received within an upper horizontal portion of the chamber 60 and the locking caps 20 received in a vertical portion of the chamber 60. The housing 58 is shown to extend perpendicularly from the barrel 46 with the chamber 60 of the housing 58 aligned with the lateral passage 56 of the barrel 46 so that the plate 44 is movable from the chamber 58 of the housing 58 into the lateral passage 56 of the barrel 46 in such a way that one of the locking caps 20 is positioned in the longitudinal passage 54 of the barrel 46. The perpendicular extension of the housing 58 relative to the barrel 46 also permits the housing 58 to serve as a handle.

Figure 17:
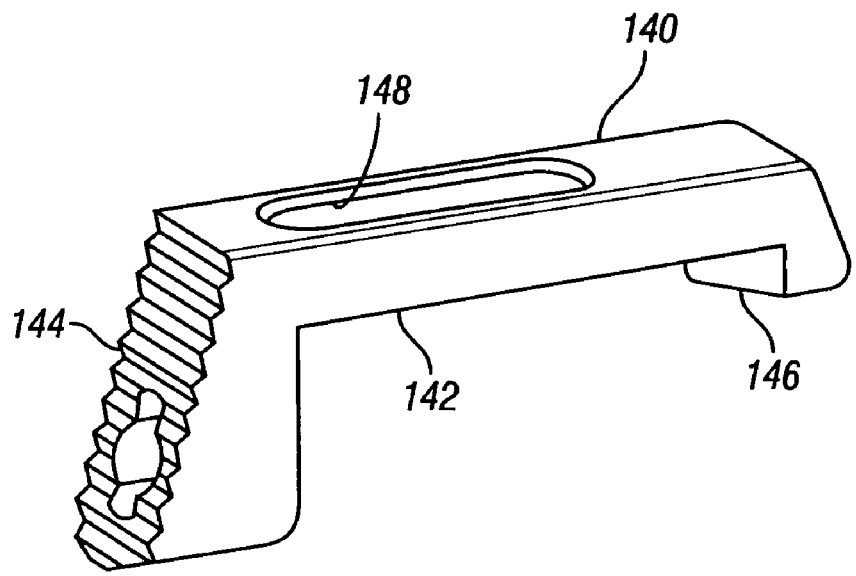
FIG. 17 is a perspective view of a retainer.
Figure 18:
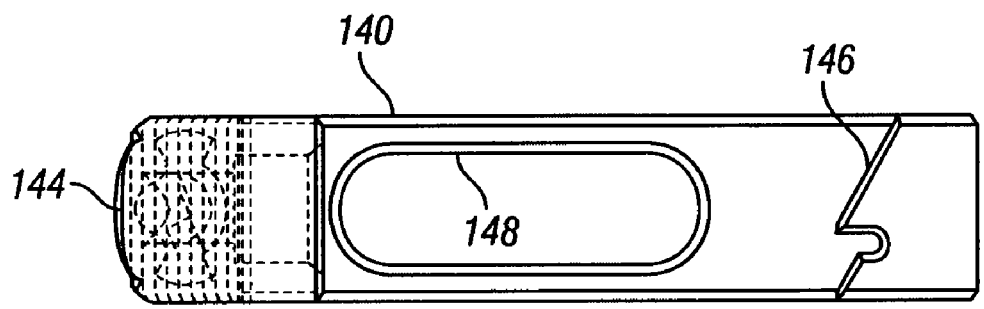
FIG. 18 is a bottom plan view of the retainer of FIG. 17.
Figure 19:
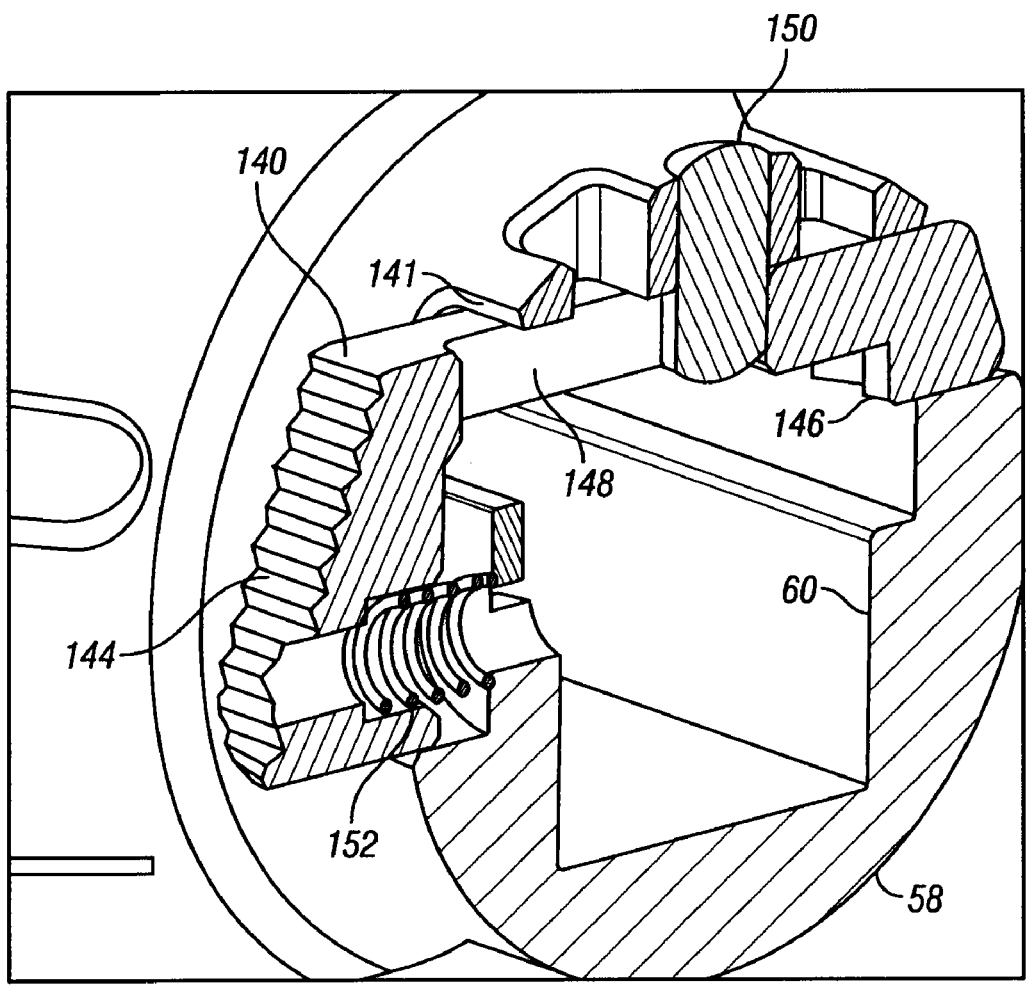
FIG. 19 is a partially cutaway, perspective view of the retainer shown positioned in the magazine and in a retaining position.
Figure 20:
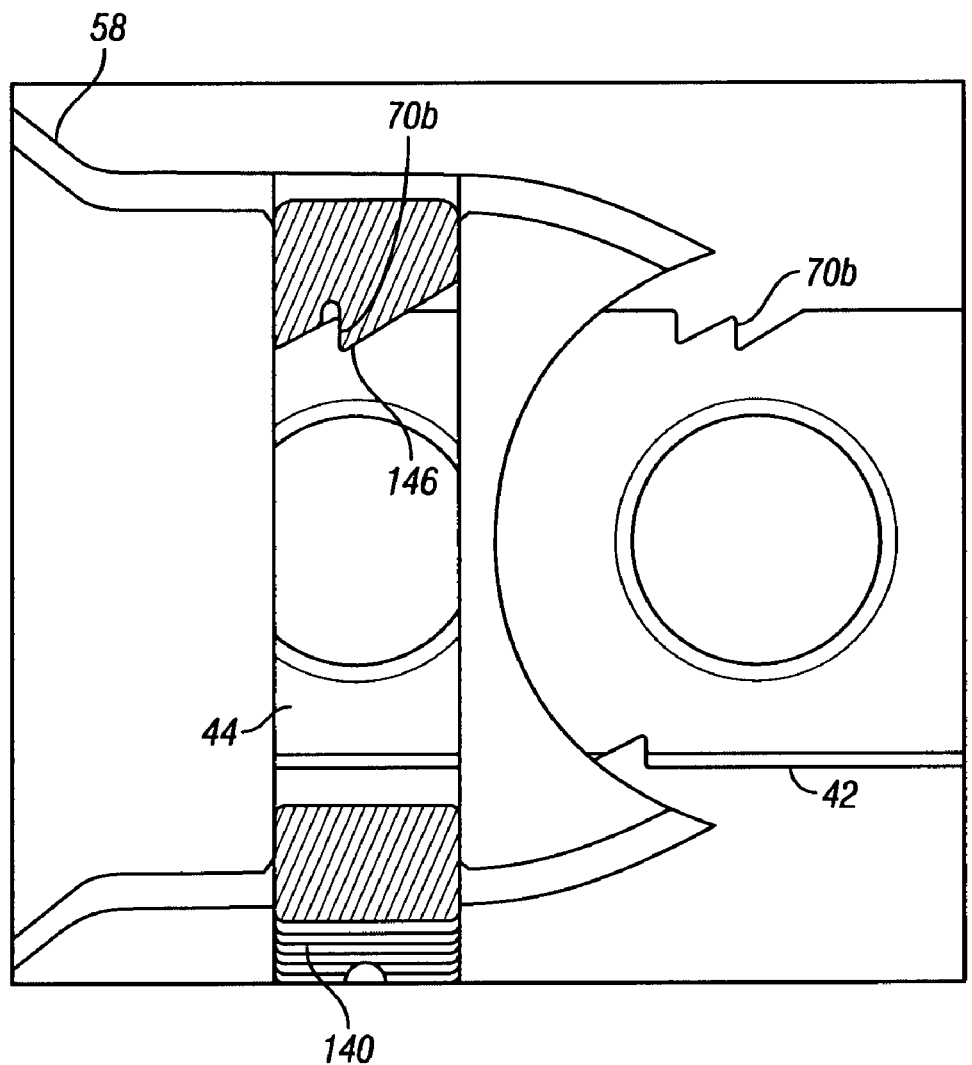
FIG. 20 is a partially cutaway, top view of the magazine illustrating the retainer in the retaining position.
Figure 21:
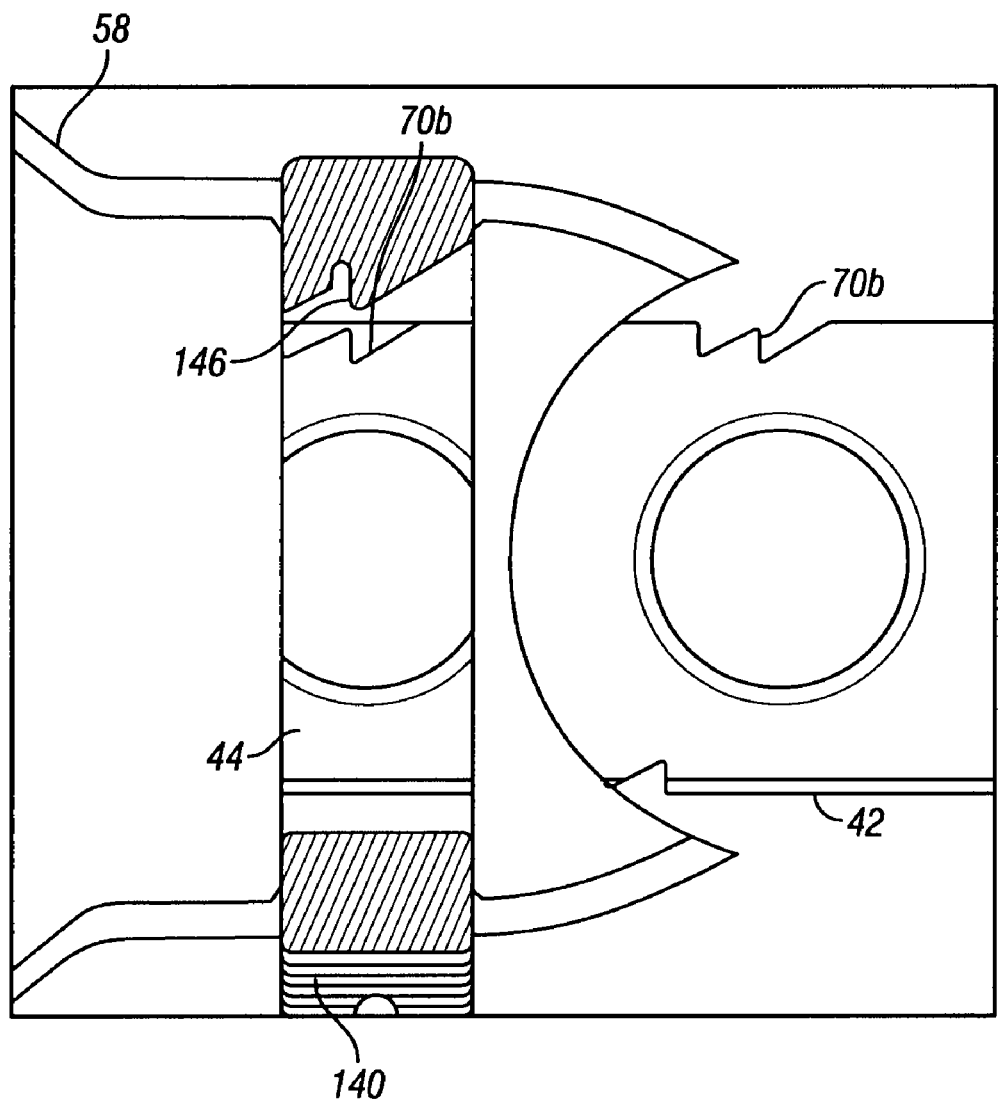
FIG. 21 is a partially cutaway, top view of the magazine illustrating the retainer in a non-retaining position.

Referring now to FIGS. 4 and 19-21, the magazine 46 includes a pusher 136 and a spring 138 disposed in the upper horizontal portion of the chamber 60 of the housing 58 to urge the locking cap clip 42 through the lateral passage 56 of the barrel 46. To hold the locking cap clip 42 in a selected position, the magazine 48 further comprises a retainer 140 disposed in a lateral slot 141 formed in the housing 58. As shown in FIGS. 17 and 18, the retainer 140 has an elongated body 142 with a push button portion 144 formed on one end and a plate engaging portion 146 formed on an opposing end. The body 142 further includes a slot 148 positioned between the push button portion 144 and the plate engaging portion 146. As best shown in FIG. 19, the retainer 140 is supported in the lateral slot 141 with a retaining pin 150 and a spring 152. The retaining pin 150 is secured to the housing 58 so as to extend into the slot 148 of the retainer 140 and the spring 152 is positioned between the housing 58 and the push button portion 144 of the retainer to urge the retainer 140 in a plate engaging position. More particularly, the retainer 140 is supported in the housing 58 so that the retainer 140 is movable between a retaining position (FIG. 20) wherein the plate engaging portion 146 of the retainer 140 engages one of the latching areas 68, 70a, 70b of the plate 44 to hold the locking cap clip 42 in a selected position and a non-retaining position (FIG. 21) wherein the plate engaging portion 146 of the retainer 140 is disengaged from the latching areas 68, 70a, 70b of the plate 44. While the plate engaging portion 146 of the retainer 140 is shown to include a pair of angled teeth matingly engageable with the latching areas 68, 70a, 70b of the plate 44, it will be appreciated by those of ordinary skill in the art that the latching areas 68, 70a, 70b and the plate engaging portion 146 may be formed to have a variety of shapes so long as they cooperate to hold the locking cap clip 42 in a desired position.

The materials used to construct the locking cap dispenser 40 are those which have sufficient strength and biocompatability, and are well known in the art for such devices. By way of example only, suitable materials include titanium, titanium alloys including Nitinol, and stainless steel. The locking cap dispenser 40 is intended to be cleaned, re-sterilized and used in multiple procedures.

Operation

With particular reference to FIGS. 22-25, a surgeon selects a desired extension number 84 and connects the extension number 84 to the barrel base 80. A locking cap clip 42 having the desired size and number of locking caps 20 is then selected. To load the locking cap clip 42 into the magazine 48, the user moves the slide member 82 from the closed position (FIG. 2) to the open position (FIG. 22) thereby causing the slide lock assembly 110 to support the slide member 82 with the open sided portion 94 of the barrel base 80 exposed. With the slide member 82 supported in the open position, the locking cap clip 42 may be inserted through the open side portion 94 of the barrel base 80 through the opening 92 of the barrel base 80, and into the chamber 60 of the housing 58 until the one of the latching areas 68 or 70 is captured by the retainer 140. With the locking cap clip 42 secured in the magazine, the slidelock assembly 110 is disengaged from the slide member 82 causing the slide member 82 to return to the closed position.

Prior to inserting the locking cap clip 42 into the chamber 60 of the housing 58, the user selects whether the locking cap clip 42 will advance through the chamber 60 in an automatic fashion or a semi-automatic fashion. More specifically, by inserting the locking cap clip 42 into the chamber 58 with the side of the plate 44 containing the latching area 68 positioned adjacent the plate engaging portion 146 of the retainer 140, the locking cap clip 42 will advance automatically upon the user securing one of the locking caps 20 to the rod receiving head 16 in a manner to be described hereinafter. In the automatic mode, the plate 44 is initially captured during the loading process by the retainer 140 at the latching area 68. The latching area 68 is positioned on the plate 44 such that the locking cap 20 positioned in or near the barrel 46 is spaced a distance from the interior surface 97 of the slide member 82.

Afterwards, the push button portion 144 of the retainer 140 is pushed to move the retainer 140 to the non-retaining position wherein the retainer 140 is disengaged from the plate 44 thereby causing the plate 44 to be advanced through the chamber 60 by the pusher 136 until the locking cap 20 positioned in the longitudinal passage 54 of the barrel 46 contacts the interior surface 97 of the slide member 82.

Figure 24:
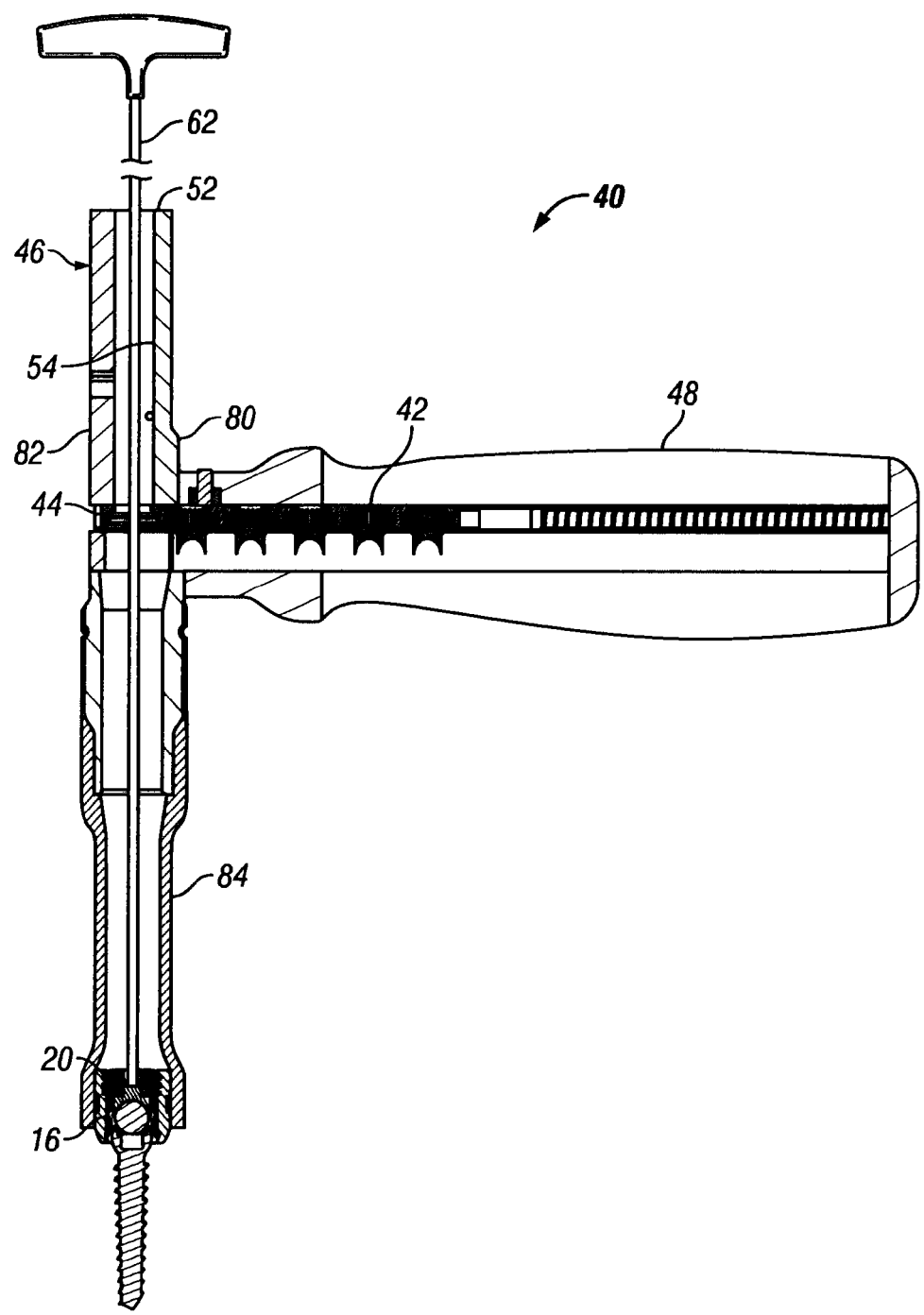
FIG. 24 is a sectional view of the locking cap dispenser shown engaging the rod receiving head and shown with the drive tool and the locking cap disposed through the barrel and connected to the rod receiving head.
Figure 25:
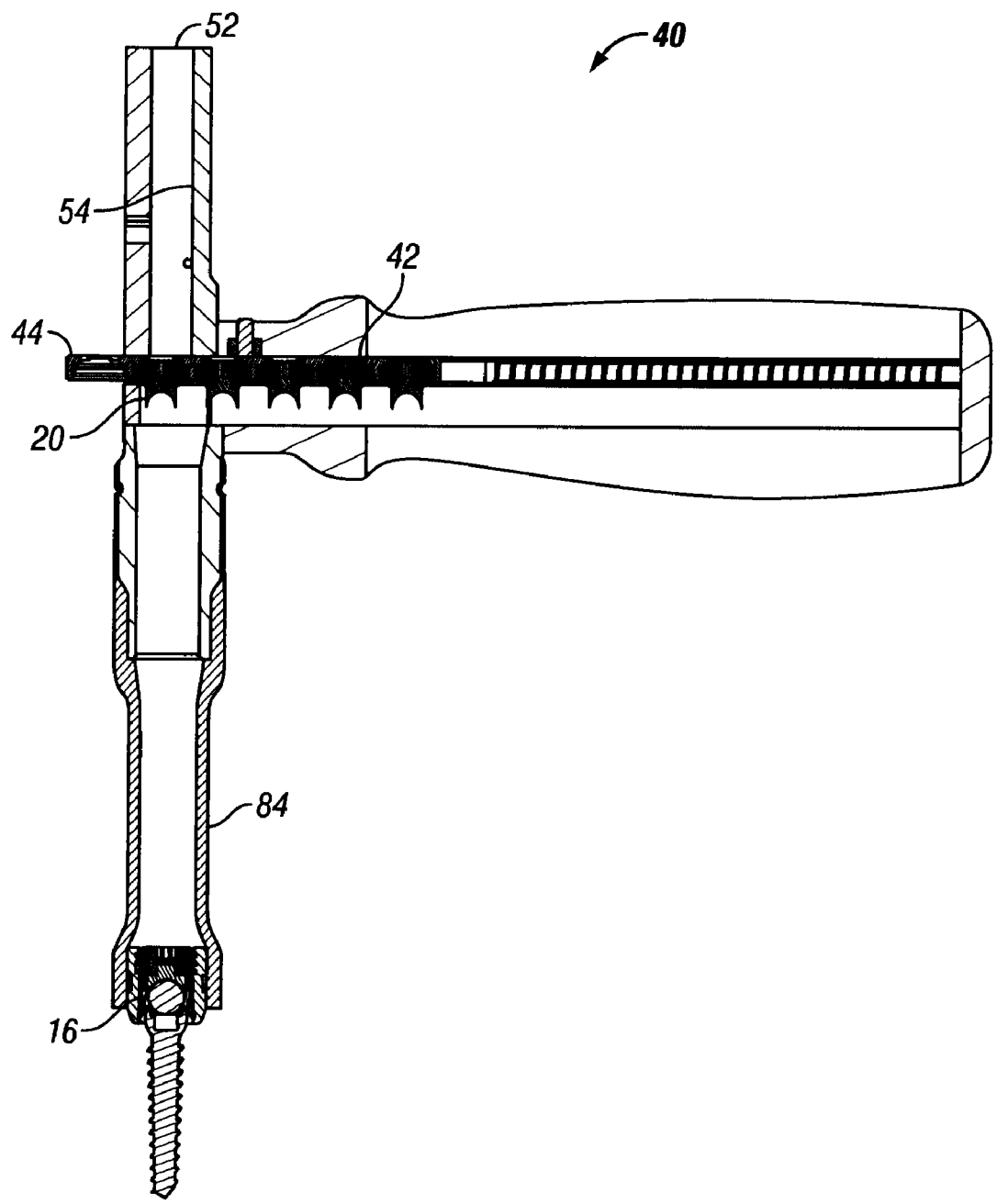
FIG. 25 is a sectional view of the locking cap dispenser shown engaging the rod receiving head and the locking cap clip advanced to position another locking cap in the barrel.

With a locking cap 20 positioned in the longitudinal passage 54 of the barrel 46, the user positions the second open end 52 of the barrel 46 over the rod receiving head 16, as well as the rod 12 positioned therein. Next, an appropriately sized drive tool 62, such as a screwdriver, is positioned through the first open end 50 and into engagement with the locking cap 20. With the drive tool 62 engaged with the locking cap 20, the locking cap 20 is substantially centered in the longitudinal passage 54 and the drive tool 62 is rotated to unthread the locking cap 20 from the plate 44. The unthreaded locking cap 20 is then moved through the longitudinal passage 54 with the drive tool 62 so as to cause the unthreaded locking cap 20 to seat with the rod receiving head 16, as shown in FIG. 24. The drive tool 62 is then rotated to apply a rotational force to the locking cap 20 to thread the locking cap 20 to the rod receiving head 16. As the locking cap 20 is being threaded to the rod receiving head 16, an axial force may be applied to the magazine 48 so as to provide a rotational force to the rod receiving head 16 that is counter to the rotational force applied to the locking cap 20 by the drive tool 62.

After the locking cap 20 has been secured to the rod receiving head 16, the drive tool 62 may be pulled back through the longitudinal passage 54 so that the tip of the drive tool 62 is withdrawn from the plate 44. In the automatic mode, the plate 44 will advance upon the drive tool 62 being withdrawn from the opening 64 of the plate 44 until the next locking cap 20 contacts the interior surface 97 of the slide member 82. The spent portion of the plate 44 advance out of the locking cap dispenser 40 through the opening 96 of the slide member 82. The process is then repeated for every locking cap 20 attached to the plate 44. After the final locking cap 20 is removed from the plate 44, the user may remove the spent plate 44 by pulling the exposed portion of the plate 44 from locking cap dispenser 40.

In the semiautomatic mode, the above described procedure is substantially the same with the exception that the locking cap clip 42 is inserted into the chamber 60 of the housing 58 with the latching areas 70a and 70b positioned adjacent the plate engaging portion 146 of the retainer 140. As such, in the semi-automatic mode, the plate 44 is initially captured at the latching area 70a in a manner similar to the plate 44 being captured at the latching area 68 in the automatic mode. In addition, upon removing the drive tool 62 from the plate 44 after the locking cap 20 has been secured to the rod receiving head 16, the plate 44 will not advance through the chamber 60 until the user pushes the retainer 140 to disengage the retainer 140 from the latching areas 70b. It will be appreciated by those of ordinary skill in the art that use of the locking cap clip 42 in the semiautomatic mode allows the longitudinal passage 54 to remain open to facilitate adjustment of previously inserted locking caps 20.

From the above description, it is clear that the inventive concepts disclosed and claimed herein are well adapted to carry out the objects and to attain the advantages mentioned herein, as well as those inherent in the invention. While exemplary embodiments of the inventive concepts have been described for purposes of this disclosure, it will be understood that numerous changes may be made which will readily suggest themselves to those skilled in the art and which are accomplished within the spirit of the inventive concepts disclosed and/or as defined in the appended claims For example, it is contemplated that the magazine may be constructed to load and receive the locking cap at a distal end of the magazine, or the locking cap clip may include a circular plate that revolves through the barrel.

What is claimed is:

1. An apparatus in combination with a locking cap clip including a plate with a plurality of threaded openings and a plurality of locking caps threadingly connected to the threaded openings of the plate, the locking caps being threadingly engageable with a rod receiving head, the apparatus comprising:
 a barrel having a first open end, a second open end, and a longitudinal passage extending through the barrel from the first open end to the second open end, the barrel further having a lateral passage extending through the barrel and intersecting the longitudinal passage; and
 a magazine having a housing with a chamber shaped to receive the locking cap clip, the housing extending from the barrel with the chamber of the housing aligned with the lateral passage of the barrel so that the locking cap clip is movable from the chamber of the housing into the lateral passage of the barrel in such a way that one of the locking caps is positioned in the longitudinal passage of the barrel so as to be matingly engageable with a drive tool insertable through the longitudinal passage to permit the drive tool to be used to unthread the locking cap from the plate and transport the unthreaded locking cap to the second open end of the barrel.

2. The combination of claim 1 wherein the second open end of the barrel is configured to lockingly engage the rod receiving head to permit a rotational force to be applied to the rod receiving head that is counter to the rotational force applied to the locking cap by the drive tool when the second open end of the barrel is lockingly engaged with the rod receiving head.

3. The combination of claim 2 further comprising a pusher disposed in the chamber of the housing to urge the locking cap clip through the lateral passage of the barrel.

4. The combination of claim 3 wherein the elongated plate has at least one notched area along one side thereof, and wherein the magazine further comprises a retainer disposed in the housing and movable between a retaining position wherein a portion of the retainer engages the plate to hold the locking cap clip in a selected position and a non-retaining position wherein the retainer is disengaged from the plate.

5. The combination of claim 4 wherein the plate further comprises a plurality of notched areas formed along one side of the plate, each of the notched areas corresponding with one of the threaded openings of the plate.

6. The combination of claim 4 wherein the plate further comprises a single notched area formed on one side of the plate and a plurality of notched areas formed along an opposing side of the plate, each of the plurality of notched areas corresponding with one of the threaded openings of the plate.

7. The combination of claim 1 the plate of the locking cap clip is elongated and wherein the threaded holes are spaced along a longitudinal axis of the elongated plate.

8. The combination of claim 1 wherein the barrel comprises:
 a barrel base connected to the magazine and having an opening defining a first portion of the lateral passage and an open side portion sized to receive the locking cap clip; and
 a slide member having an opening defining a second portion of the lateral passage of the barrel, the slide member movable along the barrel base between an open position wherein at least a portion of the open side of the barrel base is exposed to permit the locking clap clip to be inserted through the first portion of the lateral passage of the barrel and into the chamber of the housing and a closed position wherein the slide member is positioned to cover the open side portion of the barrel base and the opening of the slide member is aligned with the opening of the barrel base.

9. The combination of claim 1 wherein the barrel further comprises a tubular extension member having a proximal end connected to the barrel base and a distal end configured to engage the rod receiving head.

10. The combination of claim 1 wherein the housing of the magazine is a handle.

11. A method of securing a locking cap to a rod receiving head, comprising:
 obtaining an apparatus comprising:
  a barrel having a first open end, a second open end, and a longitudinal passage extending through the barrel from the first open end to the second open end, the barrel further having a lateral passage extending through the barrel and intersecting the longitudinal passage; and
  a magazine having a housing with a chamber, the housing extending from the barrel with the chamber of the housing open to and aligned with the lateral passage of the barrel;
 loading the chamber of the magazine with a locking cap clip comprising a plate with a plurality of threaded openings and a plurality of locking caps threadingly connected to the threaded openings of the plate, the locking caps being threadingly engageable with the rod receiving head;
 capturing the rod receiving head with the second open end of the barrel;
 advancing the plate through the chamber to cause one of the locking caps to be positioned in the longitudinal passage of the barrel;
 positioning a drive tool through the first open end of the barrel and into engagement with the locking cap;
 rotating the drive tool to unthread the locking cap from the plate;
 moving the unthreaded locking cap through the longitudinal passage with the drive tool so as to cause the unthreaded locking cap to contact the rod receiving head; and
 rotating the drive tool to apply a rotational force to the locking cap to thread the locking cap to the rod receiving head.

12. The method of claim 11 further comprising the step of advancing the plate through the chamber comprises:
 urging the locking cap clip through the lateral passage of the barrel; and
 capturing the locking cap clip to in a position wherein one of the locking caps threaded to the plate is positioned in the longitudinal passage of the barrel.

13. The method of clam 12 wherein the step of capturing the locking cap clip comprises contacting an interior surface of the barrel with the locking cap positioned in the longitudinal passage of the barrel.

14. The method of claim 13 wherein the lateral passage of the barrel includes a first portion shaped to receive the lock cap clip and a second portion shaped to receive only the plate of the locking cap clip, and wherein the step of capturing the locking cap clip further comprises urging the locking cap clip through the first portion of the lateral passage so as to cause one of the locking caps to contact an interior surface of the barrel while at least a portion of the plate extends through the second portion of the lateral passage of the barrel.

15. The method of claim 14 wherein the step of capturing the locking cap clip further comprises inserting the drive tool through one of the holes of the plate upon unthreading the locking cap from the plate.

16. The method of claim 15 wherein the step of advancing the locking cap clip comprises withdrawing the drive tool from the hole of the plate thereby causing the locking cap clip to be urged through the lateral passage until another locking cap contacts the interior surface of the barrel.

17. The method of claim 12 wherein the plate has a plurality of notched areas formed along one side of the plate, each of the notched areas corresponding with one of the threaded openings of the plate, and wherein the step of capturing the locking cap clip comprises the step of engaging the notched areas of the plate.

18. The method of clam 17 wherein the step of advancing the locking cap clip comprises disengaging the notched area thereby causing the locking cap clip to be urged through the lateral passage until another notched area is engaged.

19. The method of claim 11 wherein the barrel further comprises:
a barrel base connected to the magazine and having an opening defining a first portion of the lateral passage and an open side portion sized to receive the locking cap clip; and
a slide member having an opening defining a second portion of the lateral passage of the barrel,
wherein the step of loading the chamber of the magazine with the locking cap clip comprises:
moving the slide member along the barrel base from a closed position wherein the slide member is positioned to cover the open side portion of the barrel base and the opening of the slide member is aligned with the opening of the barrel base to an open position wherein at least a portion of the open side of the barrel base is exposed;
inserting the locking cap clip through the open side of the barrel base, through the first portion of the lateral passage of the barrel, and into the chamber of the housing; and
moving the slide member along the barrel base from open position to the closed position.

\* \* \* \* \*